(12) United States Patent
Dreyfuss

(10) Patent No.: US 8,986,346 B2
(45) Date of Patent: Mar. 24, 2015

(54) WEDGE KNOTLESS SUTURE ANCHOR

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 707 days.

(21) Appl. No.: 13/293,659

(22) Filed: Nov. 10, 2011

(65) Prior Publication Data

US 2012/0290003 A1 Nov. 15, 2012

Related U.S. Application Data

(60) Provisional application No. 61/412,442, filed on Nov. 11, 2010.

(51) Int. Cl.
 *A61B 17/04* (2006.01)

(52) U.S. Cl.
 CPC ..... *A61B 17/0401* (2013.01); *A61B 2017/0403* (2013.01); *A61B 2017/0409* (2013.01); *A61B 2017/0412* (2013.01); *A61B 2017/044* (2013.01); *A61B 2017/0451* (2013.01); *A61B 2017/0461* (2013.01)
 USPC .......................................... 606/232; 606/304

(58) Field of Classification Search
 CPC ................... A61B 17/0401; A61B 2017/0403; A61B 2017/0409; A61B 2017/0412; A61B 2017/044; A61B 2017/0451; A61B 2017/0461
 USPC ............................ 606/103, 228, 232, 300, 304
 See application file for complete search history.

(56) References Cited

U.S. PATENT DOCUMENTS

| | | | |
|---|---|---|---|
| 6,585,730 B1 | 7/2003 | Foerster | |
| 6,773,450 B2 * | 8/2004 | Leung et al. | 606/232 |
| 7,329,272 B2 | 2/2008 | Burkhart et al. | |
| 7,682,374 B2 | 3/2010 | Foerster et al. | |
| 7,892,256 B2 * | 2/2011 | Grafton et al. | 606/228 |
| 2003/0149448 A1 | 8/2003 | Foerster et al. | |
| 2006/0106423 A1 * | 5/2006 | Weisel et al. | 606/232 |
| 2006/0235413 A1 | 10/2006 | Denham et al. | |
| 2006/0282081 A1 | 12/2006 | Fanton et al. | |
| 2009/0082805 A1 * | 3/2009 | Kaiser et al. | 606/228 |
| 2009/0292321 A1 | 11/2009 | Collette | |

FOREIGN PATENT DOCUMENTS

| WO | WO 97/30649 A1 | 8/1997 |
|---|---|---|
| WO | WO 2007/078281 A2 | 7/2007 |

* cited by examiner

*Primary Examiner* — Julian W Woo
(74) *Attorney, Agent, or Firm* — Dickstein Shapiro LLP

(57) ABSTRACT

A wedge knotless anchor that is suture/wire activated. The anchor includes an anchor body and at least two flexible strands attached to the body. One of the flexible strands is a tying strand (attached to tissue to be fixated) and the other strand is a locking strand having a first end (a wedge end) and a second end. The wedge end has a larger cross-section than the second end. In the "locked position," the locking strand is pulled so that the wedge end (the larger portion) is pulled into the anchor body and plugs up an opening in the anchor body, preventing movement (sliding) of the tying tissue strand which also passes through the opening.

20 Claims, 5 Drawing Sheets

WEDGE KNOTLESS SUTURE ANCHOR

CROSS-REFERENCE TO RELATED APPLICATIONS

This application claims the benefit of U.S. Provisional Application No. 61/412,442, filed Nov. 11, 2010, the entire disclosure of which is incorporated by reference herein.

FIELD OF THE INVENTION

The present invention relates to surgical devices and, in particular, to a knotless suture anchor.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors, such as the two piece Arthrex PushLock® anchor, disclosed in U.S. Pat. No. 7,329,272, have been developed to facilitate tissue fixation to bone.

It would be desirable to provide a knotless suture anchor which has a design that allows tensioning and retensioning of the anchor as necessary, while conferring great pull out strength and ease of insertion of the anchor.

SUMMARY OF THE INVENTION

The present invention provides a knotless suture anchor for fixation of soft tissue to bone with the ability to retension the suture anchor.

The knotless suture anchor of the present invention is a wedge knotless anchor that is suture or wire activated and that comprises an anchor body and at least two flexible strands attached to the body. At least one of the flexible strands is a tying strand (attached to tissue to be fixated) and at least another of the flexible strands is a locking strand having a first end (a wedge end) and a second end, wherein the wedge end is a larger portion with a width/diameter/cross-section greater than the width/diameter/cross-section of the second end.

In the "unlocked position," the wedge end (the larger portion) of the locking strand is outside of the anchor body and, thus, the tying strand is able to freely slide within the anchor body. In the "locked position," the locking strand is pulled so that the wedge end (the larger portion) is pulled into the anchor body and plugs up the cannulation of the anchor body, preventing movement (sliding) of the tying tissue strand.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The present invention provides surgical systems and methods for knotless ligament repair and fixation, such as fixation of soft tissue to bone. The suture anchor of the present invention is wedge knotless anchor that is suture/wire activated and that comprises an anchor body with at least two flexible strands extending through the body. In an exemplary embodiment, at least one of the flexible strands is a tying strand (attached to tissue to be fixated) and at least another flexible strand is a locking strand having a first end (a wedge end) and a second end, wherein the wedge end is a larger portion with a width and/or diameter and/or cross-section greater than the width and/or diameter and/or cross-section of the second end. In an exemplary embodiment, the flexible strands may be flexible suture strands, suture tapes, nitinol strands, or high-strength sutures such as FiberWire® suture, among many others.

In the "unlocked position," the wedge end (the larger portion) of the locking strand is outside of the anchor body and, thus, the tying strand is able to slide. In the "locked position," the locking strand is pulled so that the wedge end (the larger portion) is pulled into the anchor body and plugs up the cannulation of the anchor body, preventing movement and/or sliding of the tying strand.

Figure 1:
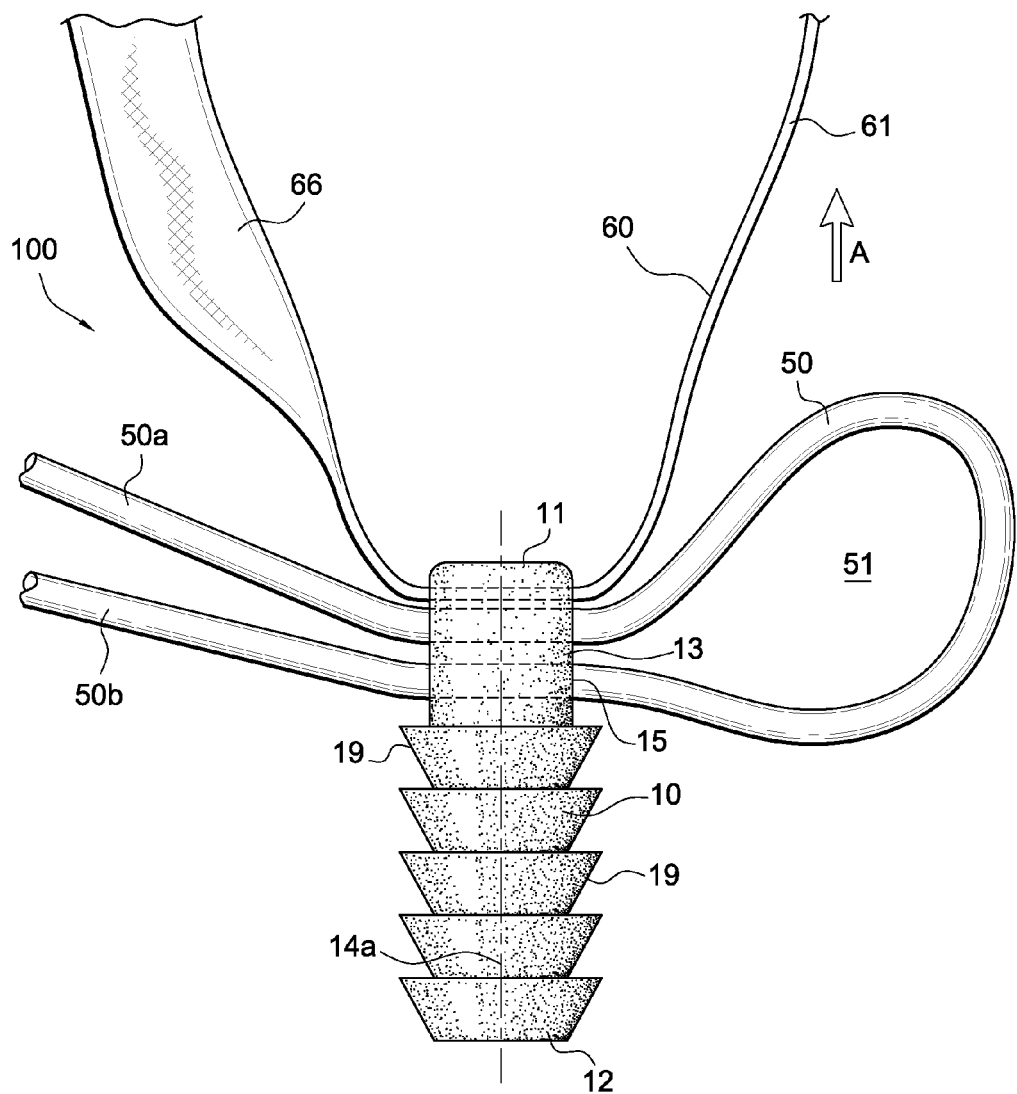
FIG. 1 illustrates a side view of a suture/wire activated wedge knotless anchor according to an exemplary embodiment of the present invention (showing the tying suture looped through tissue, and the locking/wedge suture adjacent the tying suture).
Figure 2:
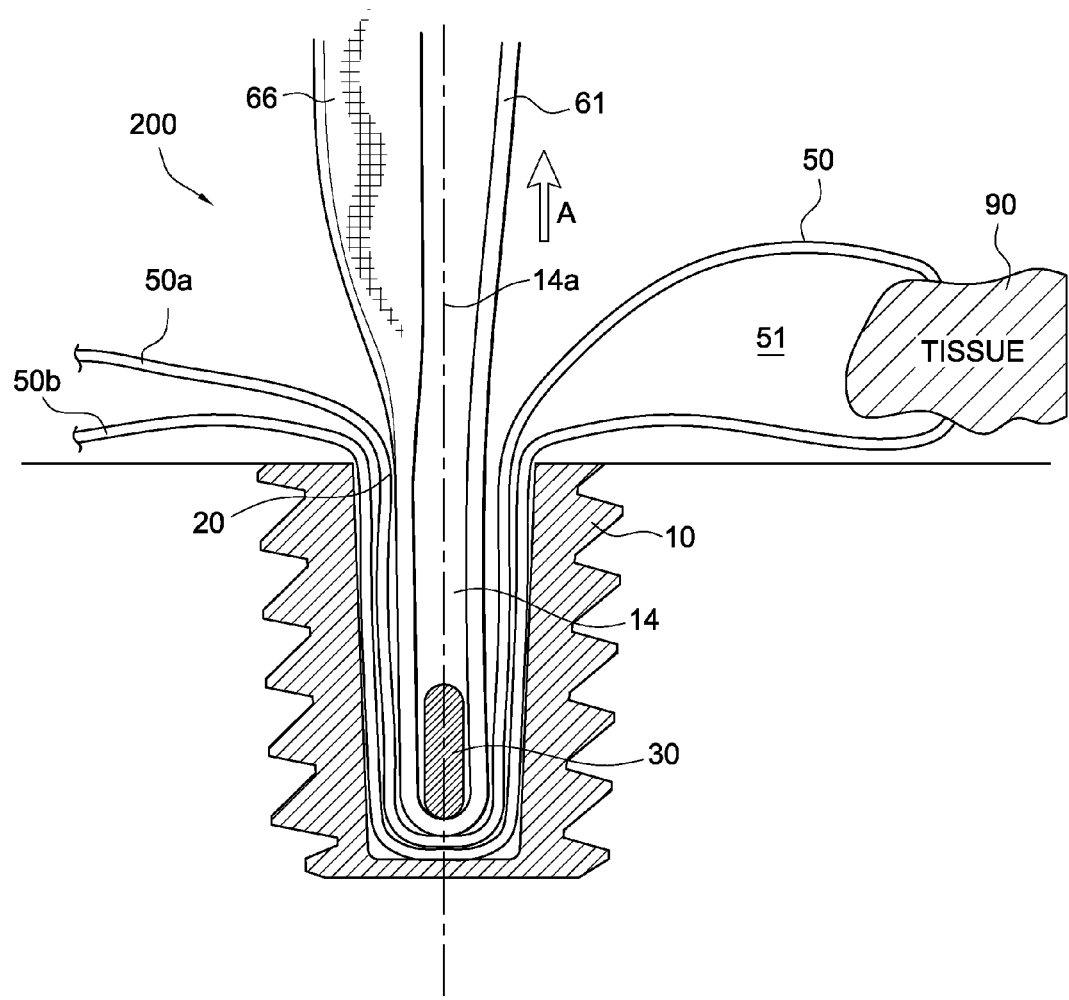
FIG. 2 illustrates a cross-sectional view of a suture/wire activated wedge knotless anchor according to another embodiment of the present invention, and in the unlocked position.
Figure 3:
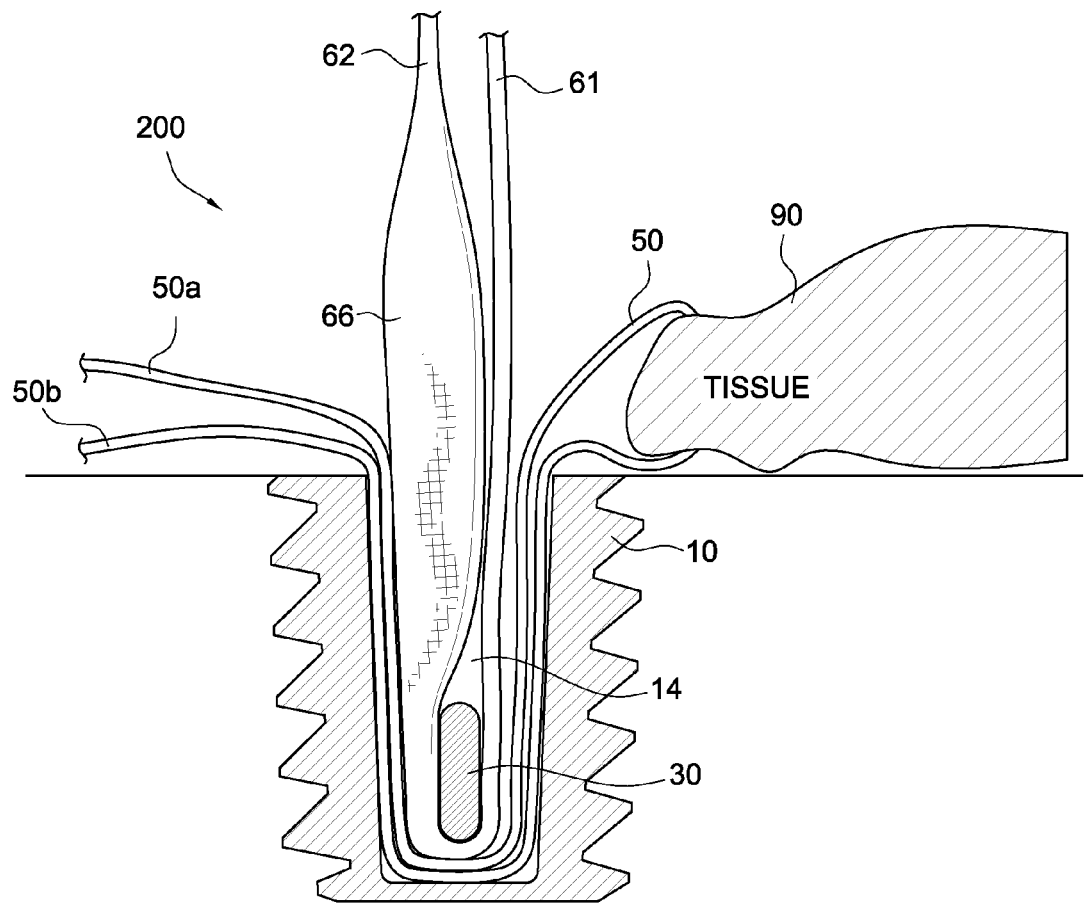
FIG. 3 illustrates a cross-sectional view of the suture/wire activated wedge knotless anchor of FIG. 2, in the locked position.

Referring now to the drawings, where like elements are designated by like reference numerals, FIGS. 1-3 illustrate exemplary wedge knotless anchors 100, 200 of the present invention. FIG. 1 illustrates exemplary wedge knotless anchor 100 without a post construct while FIGS. 2 and 3 illustrate exemplary wedge knotless anchor 200 with at least one post construct.

Wedge knotless anchor 100 of FIG. 1 is provided with an integral body 10 (anchor or implant 10) having a proximal end 11 and a distal end 12, and two flexible strands 50, 60 extending at least partially within the anchor body 10. In an exemplary embodiment, the two flexible strands 50, 60 extend about across the proximal end 11 (as shown in FIG. 1), i.e., about perpendicular to longitudinal axis 14a of the anchor body 10. As described in more detail below, and with reference to another exemplary embodiment, the flexible strands 50, 60 may also extend along at least a portion of longitudinal axis 14a of the body 10 (as shown in FIGS. 2 and 3), so that the flexible strands are moveable within lumen 14 of the body 10 (i.e., body 10 is configured to allow axial movement of the flexible strands within the lumen 14).

Proximal end 11 is provided with a drive head 13 having at least one suture eyelet 15 that allows the two flexible strands to pass therethrough. Channels 15a are also formed along either side of the drive head 13 to accommodate the flexible strands, as detailed below.

Body 10 may be provided with a plurality of ribs 19 having a truncated, conical shape, as shown in FIG. 1. Body 10 may also have various configurations and geometries such as, for example, a corkscrew configuration with a thread spiraling helically around the central body and having a configuration that facilitates insertion of the suture anchor into the bone by providing a gradual change from a starting pitch (i.e, a thread disposed along the longitudinal axis of the suture anchor at the distal end of the anchor) to a helical or spiral pitch around the central body 10. By providing the starting pitch at the distal end of the suture anchor, the suture anchor 100 can be inserted more readily into the bone without the need for additional or excessive force.

The body 10 may also have a distal end terminating in a conical, unthreaded tip terminating in a sharp point (and adjacent a threaded body), to allow easy installation of the anchor into the bone and with less tissue material displacement upon insertion.

Flexible strand 50 shown in FIG. 1 may be a tying suture that is attached to tissue 90 (for example, looped through tissue to form a loop 51 as shown in FIG. 2) with free ends 50*a*, 50*b* of the tying strand 50 passing through the proximal end 11 of the anchor body (as shown in FIG. 1). Flexible strand 60 may be a locking, strand with two ends: a first end 62 (not shown) with a wedge portion or wedge end 66 (that gets pulled into the eyelet 15 to fix the construct) and a second end 61 (that gets pulled to lock the tying suture 50 within the eyelet). The wedge end 66 is an enlarged end relative to the second end 61, i.e., the diameter/width/cross-section of the wedge end 66 is greater than the diameter/width/cross-section of the end 61.

FIG. 1 illustrates wedge knotless anchor 100 in the "unlocked position." In this position, the wedge end 66 (the larger, wider, thicker portion) of the locking suture 60 is located outside of the anchor body 10 and, thus, the tying strand 50 is able to freely slide within the proximal end 11 of the anchor body.

In the "locked position," end 61 of the locking suture 60 is pulled in the direction of arrow A of FIG. 1, so that the wedge end 66 (the larger portion) is pulled inside the anchor body 10 and plugs up the proximal end 11 (i.e., because of its enlarged cross-section and dimension, the wedge end 66 compresses the tying suture 50 and restricts movement and sliding of the tying suture 50 within the proximal end).

By pulling on the other end 62 of the locking suture 60, the construct is released, the wedge end 66 is pulled out of the proximal end 11, the tying suture 50 is decompressed and, thus, movement of the tying suture 50 within proximal end 11 is restored.

FIGS. 2 and 3 illustrate another exemplary embodiment of wedge knotless anchor 200 provided with an integral body 10 (anchor or implant 10) having a proximal end 11 and a distal end 12, and two flexible strands 50, 60 extending at least partially within the anchor body 10. In this exemplary-only embodiment, the two flexible strands 50, 60 extend along at least a portion of longitudinal axis 14*a* of the body 10, so that the flexible strands are movable within lumen 14 of the body 10. This embodiment allows axial movement of the flexible strands 50, 60 within the lumen 14.

As in the previous embodiment, proximal end 11 may be provided with a drive head to allow engagement with a driver (for example, a hand driver) for insertion of the anchor within a bone.

Body 10 may have various configurations and geometries such as, for example, a corkscrew configuration with a thread spiraling helically around the central body and having a configuration that facilitates insertion of the suture anchor into the bone by providing a gradual change from a starting pitch (i.e, a thread disposed along the longitudinal axis of the suture anchor at the distal end of the anchor) to a helical or spiral pitch around the central body 10. By providing the starting pitch at the distal end of the suture anchor, the suture anchor 100 can be inserted more readily into the bone without the need for additional or excessive force.

The body 10 may also have a distal end terminating in a conical, unthreaded tip terminating in a sharp point (and adjacent a threaded body), to allow easy installation of the anchor into the bone and with less tissue material displacement upon insertion.

Flexible strand 50 shown in FIGS. 2 and 3 may be a tying suture that is attached to tissue 90 (for example, looped through tissue to form a loop 51 as shown in FIG. 2) with free ends 50*a*, 50*b* of the tying strand 50 exiting opening 20 of the proximal end 11. In use, one of the free ends 50*a*, 50*b* is passed into the lumen 14 through opening 20 at the proximal end 11, and then looped around post 30 (turning post 30) located at the distal end 12, and then passed out of the lumen 14 through the opening 20 at the proximal end 11.

Flexible strand 60 may be a locking strand with two ends: a first end 62 with a wedge portion or wedge end 66 (that gets pulled into the eyelet 15 to fix the construct) and a second end 61 (that gets pulled to lock the tying suture 50 within the eyelet). The wedge end 66 is an enlarged end relative to the second end 61, i.e., the diameter and/or width and/or cross-section of the wedge end 66 is greater than the diameter and/or width and/or cross-section of the end 61. In use, the second end 61 of the strand 60 is passed into the lumen 14 through opening 20 at the proximal end 11, and then looped around post 30 (turning post 30) located at the distal end 12 so that the second end 61 is adjacent the suture strand 50, and then passed out of the lumen 14 through the opening 20 at the proximal end 11.

FIG. 2 illustrates the wedge knotless anchor 200 in the "unlocked position." In this position, the wedge end 66 (the larger, wider, thicker portion) of the locking suture 60 is located outside of the anchor body 10 and, thus, the tying strand 50 is able to freely slide around post 30 within the anchor body.

FIG. 3 illustrates the wedge knotless anchor 200 in the "locked position." In this position, end 61 of the locking suture 60 is pulled in the direction of arrow A of FIG. 2, so that the wedge end 66 (the larger portion) is pulled inside the anchor body 10 and plugs up the cannulation or lumen 14 (and turning post 30), preventing therefore the movement (sliding) of the tissue tying suture 50. In the "locked position" or "locked configuration" shown in FIG. 3, the wedge end 66 is located in between the post 30 and the tying strand 50 and, as a result of the compression exercised upon the tying strand 50, the wedge end 66 is also in contact with the post 30 and the tying strand 50. In this manner, the enlarged portion of the locking suture 60 prevents movement of the tying strand within the lumen 14 of the anchor body 10 and locks the tying strand 50. By pulling on the other end 62 of the locking suture 60, the construct is released, the wedge end 66 is disengaged from the post 30 and the tying suture 50 located around the post and, thus, movement of the tying suture 50 within lumen 14 is restored.

Although FIGS. 1-3 illustrate only one tying suture 50, the invention also contemplates a plurality of tying sutures 50. Although FIGS. 2 and 3 illustrate anchor 200 provided with one turning post 30, the invention also contemplates anchors with more than one turning post, or similar structures. The invention also contemplates embodiments without such post(s) or similar structure(s), so that the wedge (the wedge end 66) is stuffed directly into the cannulation of the anchor body, without the aid of a post.

Body 10 may be formed of a bioabsorbable material such as poly(l-lactide-co-d,l-lactide) 70:30 (PLDLA), PEEK, metals or metal alloys (such as stainless steel, titanium or titanium alloys, for example), absorbable and/or nonaborbable materials, natural and/or synthetic polymers, among many others. Although body 10 of anchor 100 has been illustrated as having a ribbed configuration, the invention is not limited to this exemplary only embodiment and contemplates an anchor having different shapes and geometries, or a combination of different shapes and geometries.

At least one of flexible strands 50, 60 may be a high-strength suture, such as the high strength suture sold by Arthrex, Inc. of Naples, Fla. under the registered tradename FiberWire®, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. The suture may optionally include filaments of various colors.

At least one of strands 50, 60 may be also formed of suture tape (for example, a collagen stuffed suture tape) or a combination of suture and tape, a stiff material, or combination of stiff and flexible materials, depending on the intended application.

Figure 4:
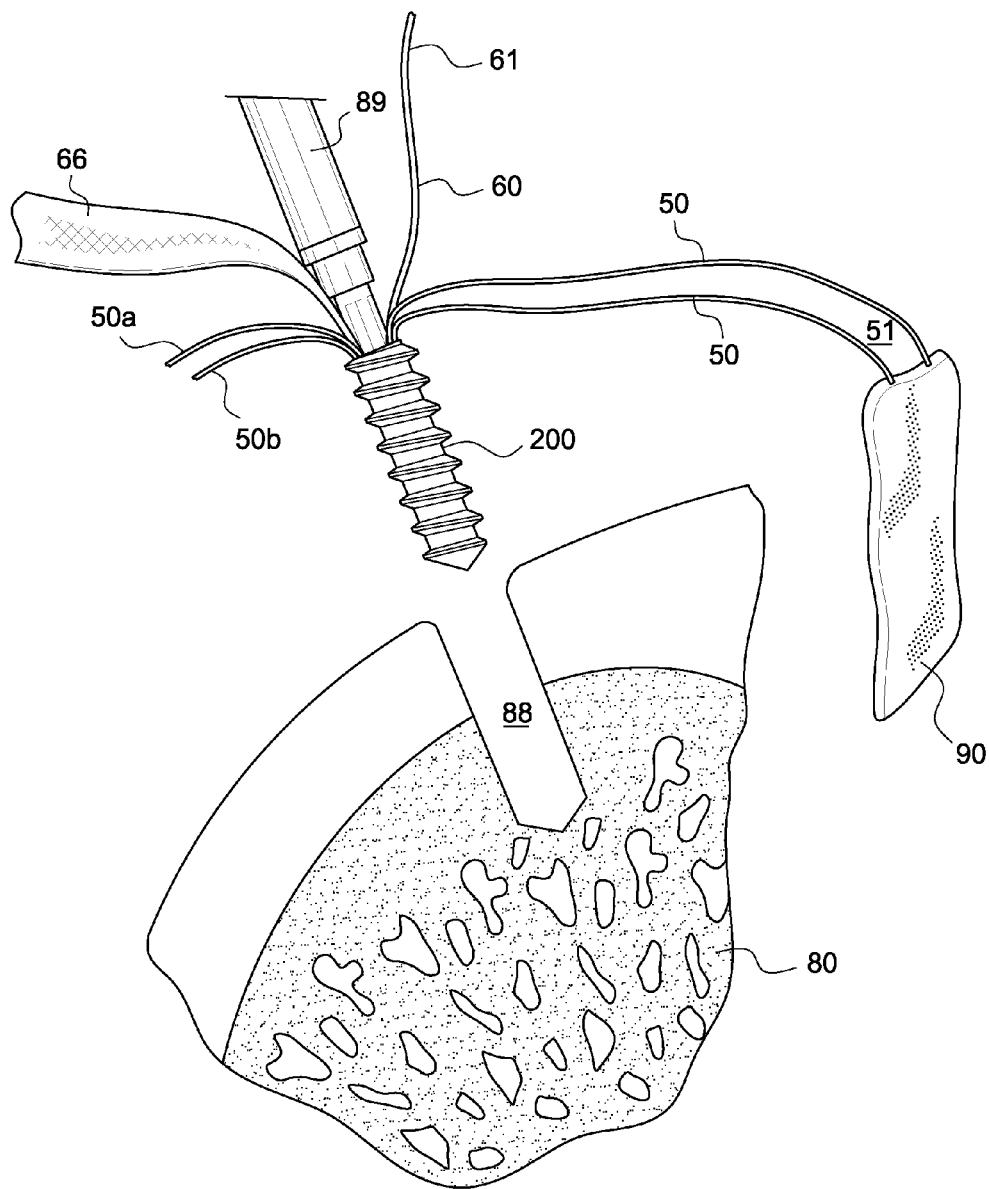
FIGS. 4 and 5 illustrate subsequent steps of a method of tissue fixation with a suture/wire activated wedge knotless anchor of the present invention.
Figure 5:
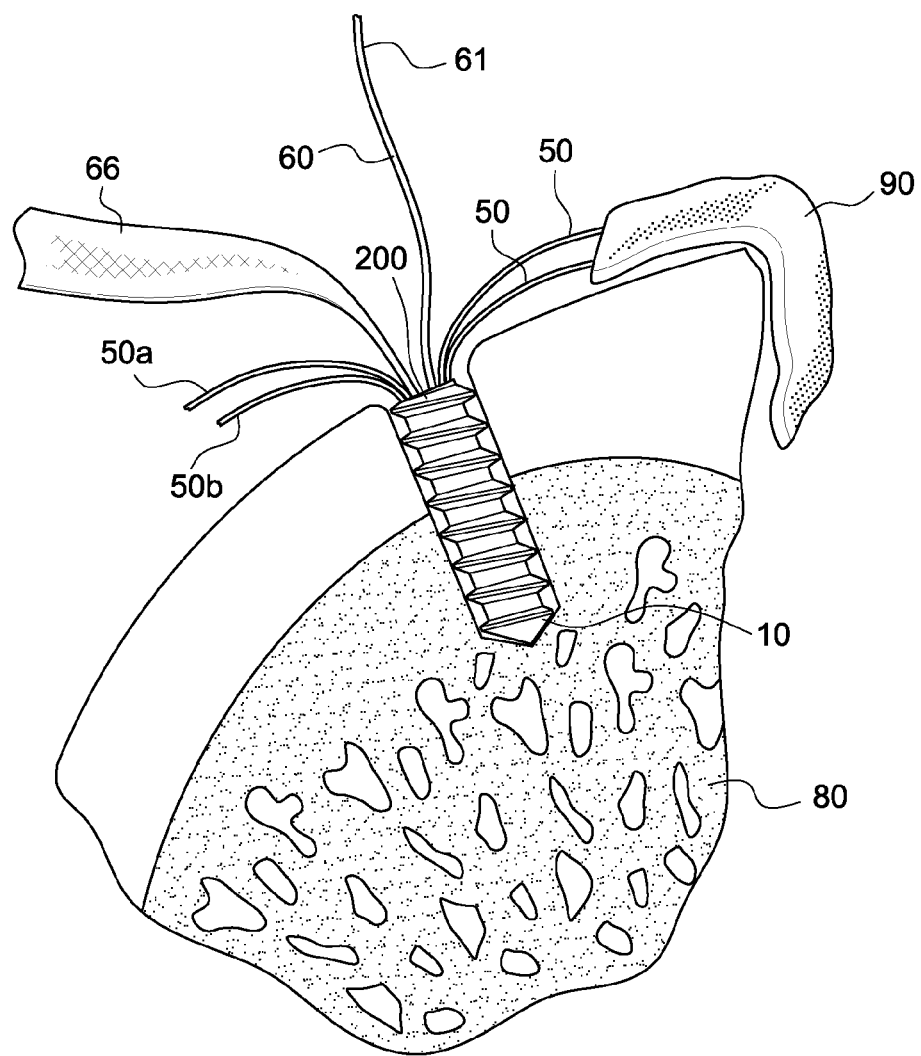

Wedge knotless anchors 100, 200 described above may be employed for tissue repairs, such as fixation of soft tissue to bone. In an exemplary embodiment only, and with reference to FIGS. 4 and 5, a pilot hole 88 is created in bone 80 by employing a punch or a drill, for example. After the pilot hole 88 is created and the punch or drill is removed, exemplary knotless suture anchor 200 is loaded onto a driver 89 (for example, a standard hand driver), as shown in FIG. 4. The knotless anchor 200 is positioned on the driver 89, and the anchor with driver is inserted into the prepared pilot hole 88 by hand. A mallet may be used to advance knotless anchor 200 into the hole. Once the knotless anchor 200 is advanced into the pilot hole, the driver handle is pulled straight off the anchor.

Tensioning/retensioning of the knotless suture anchor 200 may be achieved by pulling on the free end 61 of the strand 60, to lock or unlock the tying strand 50 attached to tissue 90 (by positioning the enlarged section 66 in contact with the post 30 and the first strand 50), as necessary and as desired.

Additional anchors may be inserted dependent upon the size of the soft tissue defect. Suture passing and knot tying are carried out in the preferred fashion to secure attachment of soft tissue to bone.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A knotless anchor for fixation of a length of a flexible material, comprising:
    an anchor body having a proximal end and a distal end, and a cannulation extending from an opening at the proximal end and within the anchor body;
    a first flexible strand disposed at least partially within the anchor body, the first flexible strand being configured to attach to tissue to be fixated; and
    a second flexible strand disposed at least partially within the anchor body and adjacent the first flexible strand, the second flexible strand having two ends, a first end with a wedge portion or wedge end, and a second end, the second flexible strand being configured to compress the first flexible strand against at least the anchor body and restrict movement of the first flexible material strand within the anchor body.

2. The knotless anchor of claim 1, wherein the second flexible strand has a first portion with a first cross-section and a second portion with a second-cross section, the first cross-section being different from the second cross-section.

3. The knotless anchor of claim 1, wherein the second flexible strand has a first portion with a first width and a second portion with a second width, the first width being different from the second width.

4. The knotless anchor of claim 1, wherein the second flexible strand has a first portion with a first diameter and a second portion with a second diameter, the first diameter being different from the second diameter.

5. The knotless anchor of claim 1, wherein the first and second flexible strands extend at least along a longitudinal portion of the anchor body.

6. The knotless anchor of claim 1, wherein the first and second flexible strands extend at least across the proximal end of the body.

7. The knotless anchor of claim 1, wherein at least one of the first and second flexible strands is a suture, a suture tape, a UHMWPE suture or a combination of suture, suture tape, or UHMWPE suture.

8. The knotless anchor of claim 1, wherein the first flexible strand is passed through the opening at the proximal end and into the cannulation of the anchor body, looped around at least one post located at the distal end, and then passed out of the cannulation of the anchor body and through the opening at the proximal end.

9. A knotless suture anchor for fixation of a length of suture, comprising:
    an anchor body having a proximal end, a distal end, a lumen opening at the proximal end, and at least one turning post extending within the anchor body and across the lumen at the distal end;
    a length of suture passed into the lumen, from the proximal end, looped around the at least one turning post at the distal end, and passed out of the lumen through the proximal end; and
    a flexible material disposed at least partially within the anchor body and adjacent the length of suture, the flexible material being located between the turning post and the length of suture, the flexible material being moveable within the lumen and configured to allow axial movement of the length of suture within the lumen when the flexible material is in a first position, and to prevent axial movement of the length of suture within the body when the flexible material is in a second position, wherein the flexible material has a first longitudinal portion which has a first cross-section and a second longitudinal portion which has a second cross-section which is larger than the first cross-section.

10. The knotless suture anchor of claim 9, wherein when the flexible material is in the second position, the second longitudinal portion of the flexible material presses the length of suture against the body and limits movement of the length of suture, and, when the flexible material is in the first position, the second longitudinal portion of the flexible material does not press the length of suture against the body and does not limit movement of the length of suture within the lumen.

11. The knotless suture anchor of claim 9, wherein the at least one turning post is a rod disposed transversally within a portion of the body and distal to the lumen opening.

12. The knotless suture anchor of claim 9, wherein the flexible material is a suture strand or a suture tape, or combination of suture strand and suture tape.

13. A method of fixating soft tissue to bone, comprising the steps of:
provide a hole in a bone at a location at which a soft tissue graft is to be affixed;
providing a suture anchor in the vicinity of the hole, the suture anchor comprising an anchor body having a proximal end and a distal end, and a cannulation extending from an opening at the proximal end and within the anchor body; a first flexible strand disposed at least partially within the cannulation of the anchor body, the first flexible strand being attached to the soft tissue graft to be fixated; and a second flexible strand disposed at least partially within the cannulation of the anchor body and adjacent the first flexible strand, the second flexible strand having two ends, a first end with a wedge portion or wedge end, and a second end, the second flexible strand being configured to compress the first flexible strand against at least the anchor body and restrict movement of the first flexible strand within the anchor body;
pulling on one end of the first flexible strand through the opening at the proximal end such that the soft tissue graft is drawn toward the hole; and
pulling on the second end of the second flexible strand to move the second flexible strand within the cannulation of the anchor body from a first position that does not interfere with movement of the first flexible strand within the anchor body to a second position that interferes with movement of the first flexible strand within the anchor body and locks the first flexible strand relative to the anchor body.

14. The method of claim 13, further comprising the steps of:
pulling on the first end of the second flexible strand to move the second flexible strand within the cannulation of the anchor body from the second position to the first position, and to allow movement of the first flexible strand within the anchor body; and
pulling on the first flexible strand to tension the suture anchor.

15. The method of claim 13, wherein the wedge portion has a first cross-section and the second end has a second-cross section, the first cross-section being different from the second cross-section.

16. A method of locking suture within a body of a knotless suture anchor, comprising the steps of:
providing a suture anchor comprising an anchor body having a proximal end, a distal end, a lumen opening at the proximal end, and a turning post extending within the anchor body and across the lumen at the distal end;
providing a length of suture at least partially within the anchor body by passing the length of suture through the opening at the proximal end and into the lumen, looping the length of suture around the turning post, and then passing out the length of suture through the lumen and out of the opening at the proximal end;
providing a length of flexible material at least partially within the anchor body and adjacent the length of suture by passing the length of flexible material through the opening at the proximal end and into the lumen, looping the length of flexible material around the turning post, and then passing out the length of flexible material through the lumen and out of the opening at the proximal end, the length of flexible material having a first portion with a first cross-section and a second portion with a second cross-section which is smaller than the first cross-section; and
pulling on the length of flexible material to prevent movement of the length of suture within the lumen and to lock the length of suture within the anchor body.

17. The method of claim 16, further comprising the steps of:
advancing the first portion with the first cross-section of the length of flexible material into the lumen of the anchor, by pulling on one end of the length of flexible material, so that the first portion is positioned in between the length of suture and the post; and
compressing the length of suture against the anchor body and against the first portion of the length of flexible material, to lock the length of suture within the anchor body.

18. The method of claim 17, further comprising the step of pulling on the other end of the length of flexible material, so that the second portion is positioned in between the length of suture and the post, and to allow movement of the length of suture within the lumen of the anchor body.

19. The method of claim 16, wherein the length of flexible material is a suture, a suture tape, a wire, or a combination of suture, suture tape, or wire.

20. The method of claim 16, wherein the length of suture is attached to tissue to be fixated within the body.

* * * * *